United States Patent [19]

Serini et al.

[11] 4,348,542
[45] Sep. 7, 1982

[54] PROCESS FOR THE PRODUCTION OF MIXTURES OF ALKYLATED AROMATIC HYDROXY COMPOUNDS

[75] Inventors: Volker Serini; Rainer Neumann; Gerhard Friedhofen; Dieter Freitag; Jürgen Heuser; Hans-Helmut Schwarz, all of Krefeld, Fed. Rep. of Germany

[73] Assignee: Bayer Aktiengesellschaft, Leverkusen, Fed. Rep. of Germany

[21] Appl. No.: 167,376

[22] Filed: Jul. 9, 1980

[30] Foreign Application Priority Data

Jul. 13, 1979 [DE] Fed. Rep. of Germany ....... 2928443

[51] Int. Cl.³ .............................................. C07C 39/12
[52] U.S. Cl. ................................... 568/727; 568/728; 568/730
[58] Field of Search ............... 568/727, 728, 730, 717, 568/196, 719

[56] References Cited

U.S. PATENT DOCUMENTS 3,049,568  8/1962  Apel et al. ........................... 568/728
3,049,569  8/1962  Apel et al. ........................... 568/728
3,221,061 11/1965  Grover et al. ....................... 568/728
3,242,219  3/1966  Farnham et al. ..................... 260/619
3,394,089  7/1968  McNutt et al. ....................... 521/32

FOREIGN PATENT DOCUMENTS 214436   4/1961  Austria .
1863     5/1979  European Pat. Off. ............. 568/728
2830174  1/1979  Fed. Rep. of Germany .
2830175  1/1979  Fed. Rep. of Germany .
883391  10/1959  United Kingdom ................ 568/728
937072   9/1963  United Kingdom .
1185102  3/1970  United Kingdom .
1185223  3/1970  United Kingdom .

Primary Examiner—Werren B. Lone
Attorney, Agent, or Firm—Connolly and Hutz

[57] ABSTRACT

A process for the production of mixtures of alkylated aromatic polyhydroxy compounds by reacting alkylated phenols with carbonyl compounds, wherein acidic organic ion exchangers are used as catalysts and commercial dialkyl phenols as the phenol and any unreacted starting phenols separated off are completely recycled into the process without intermediate purification, and the application of the thus produced polyhydroxyl compounds for making thermoplastic polycarbonates.

3 Claims, No Drawings

PROCESS FOR THE PRODUCTION OF MIXTURES OF ALKYLATED AROMATIC HYDROXY COMPOUNDS

This invention relates to a process for the production of mixtures of alkylated aromatic polyhydroxy compounds of phenols and carbonyl compounds which is characterised in that acid organic ion exchangers are used as catalysts and commerical 2,6-dialkyl phenols containing from 98 to 70% of 2,6-dialkyl phenol are used as the phenols.

The present invention also relates to the mixtures of alkylated aromatic polyhydroxy compounds obtained by the process according to the invention. They may be hydrogenated to form cycloaliphatic polyhydroxy compounds which are important, for example, in the production of polyesters. They may also be hydrogenated and aminated to form polyamines which have a minimal tendency towards crystallisation and which may be used with advantage for the synthesis of polyamides and polyurethanes and for other purposes. More particularly, they may also be used with advantage for the production of high molecular weight polycarbonates having excellent properties. Accordingly, the present invention also relates to the use of the mixtures of alkylated aromatic polyhydroxy compounds obtained in accordance with the invention for the production of high molecular weight polycarbonates and to the polycarbonates themselves. The high molecular weight polycarbonates may be produced by known methods which are described, for example, in German Offenlegungsschrifts Nos. 2,063,050; 2,063,052; 1,570,703; 2,211,956 and 2,211,957 and German Patent Applications P 29 01 665.7 and P 29 01 668.0.

On the commercial scale, 2,6-dimethyl phenol is generally obtained by alkylating phenol with methanol in the presence of inorganic catalysts (Ullmann, Encyclopadie der technischen Chemie, Supplementary Volume (1970)(185). In addition to residual unreacted phenol, 2,6-dimethyl phenol and, to a greater or lesser extent, o-cresol, p-cresol, m-cresol and other, at least bialkylated phenols are generally obtained, depending on the alkylation conditions. The 2,6-dimethyl phenol is generally separated off from the alkylate by distillation if the content of the other alkylated phenols and the unreacted phenol is too high for the purpose for which the 2,6-dimethyl phenol is to be used. Highly pure 2,6-dimethyl phenol, of the type hitherto used for the production of poly-(2,6-dimethyl phenyl) -oxide or 2,2-bis-(3,5dimethyl-4-hydroxy phenyl)-propane, can only be obtained by increased expenditure on distillation or by other expensive purifying operations, such as crystallisation for example.

In known commercial processes for alkylating phenols with methanol (Chem. Processing 1966, November, page 113 and Chem. Processing 1968, April, pages 32 to 35), 85 to 99% pure 2,6-dimethyl phenols are obtained, having to be further purified for the production of polymers.

The cost of the 2,6-dimethyl phenol increases considerably with the degree of purity because the above-mentioned purifying operations involve considerable capital outlay. Thus, the price of a 99.5% pure 2,6-dimethyl phenol is about 5 times higher than that of an approximately 90% pure material (Chem. Processing 1966, November, page 133). In general, the impurities in the technical 2,6-dimethyl phenols are mainly o-, m- and p-cresol (from 2 to 30%) in addition to small quantities of phenol (from less than 0.1 to 5%) and polyalkylated phenols (from less than 0.1 to 2%).

The other known commercially dialkylated phenols are also characterised by substantially the same impurity contents.

It is known that aromatic dihydroxy compounds can be obtained from pure phenols, such as for example phenol, o-cresol or 2,6-dimethyl phenol, and carbonyl compounds by means of acid catalysts and, optionally, S-containing co-catalysts (H. Schnell, Chemistry and Physics of Polycarbonates, New York-London-Sydney, Interscience Publishers 1964, Polymer Reviews, Vol. 9 and German Offenlegungsschrift No. 2,537,027).

The acid catalysts used may be, for example hydrogenchloride or acid organic ion exchangers as described in U.S. Pat. Nos. 3,394,089 and 3,049,568 and German Offenlegungsschrift No. 2,537,027. Ion exchangers are, for example sulphonated phenolformaldehyde resins or sulphonated polystyrenes crosslinked with from 2 to 25% by weight and preferably with from 6 to 20% by weight of divinyl benzene.

It has now surprisingly been found that it is possible completely to react commercial 2,6-dialkyl phenols containing from 70 to 98%, preferably 80 to 98% and, with particular preference, from 85 to 95% of 2,6-dialkyl phenol, preferably 2,6-dimethyl phenol, with carbonyl compounds in the presence of acid, organic ion exchangers to form alkylated aromatic polyhydroxy compounds which are suitable for the production of polycarbonates.

In cases where acid organic ion exchangers are used, the phenols alkylated to different extents in the commercial dialkyl phenols, preferably 2,6-dimethyl phenols, unexpectedly react off at substantially the same velocity to form aromatic polyhydroxy compounds.

It is also surprising that, following the removal by distillation of excess phenols and low-boiling substances and after the desorption of residual monophenols, as described in more detail hereinafter, the entire residue may be reacted without further purification to form high molecular weight high-grade polycarbonates.

Accordingly, the present invention relates to a process for the production of alkylated aromatic polyhydroxy compounds by completely reacting alkylated phenols with carbonyl compounds which is characterised in that acid organic ion exchangers are used as the acid catalysts and commercial dialkyl phenols as the phenols and the unreacted starting phenols, if any, separated off from the reaction mixture are completely reacted without being worked up again.

Accordingly, the process according to the invention has the advantage that, in the event of inclomplete reaction or in cases where the starting phenols are used in excess (U.S. Pat. Nos. 3,394,089 and 3,049,568 and German Offenlegungsschrift No. 2,537,027), the composition of the unreacted starting phenols separated off remains the same. Accordingly, they may be re-used to form consistently the same end products.

Accordingly, there is no need during the synthesis process to separate off any of the unreacted starting phenol and to replace it by fresh starting phenol.

Accordingly, there is also no need for the material separated off to be worked up again. Accordingly, the conversion of the starting phenol mixture is complete so that the yield amounts to 100%. The extremely high economy of the process results from the possiblity of completely converting commercial 2,6-dialkyl phenols of low purity into mixtures of alkylated aromatic polyhydroxy compounds, preferably alkylated aromatic dihydroxy compounds, which in addition may be worked up very simply without any losses, as described hereinafter.

Acids other than the acid organic ion exchangers do not produce the same surprising result. With hydrochloric acid for example, the concentrations of the cresols are reduced to a considerable extent so that there is no guarantee of the residual phenol having a uniform composition. With sulphuric acid for example, large quantities of sulphonated secondary products are formed, which are unsuitable for the synthesis of polycarbonates, so that there are heavy losses of material and simple working up in the manner described above is not possible.

The 2,6-dialkyl phenols used are preferably those containing from 1 to 4 carbon atoms in the alkyl groups, 2,6-dimethyl phenol being particularly preferred. The corresponding commercial 2,6-dialkyl phenols generally consist of from 98 to 70% of 2,6-dialkyl phenol, from 2 to 30% of monoalkyl phenol, from less than 0.1 to 5% of phenol and from less than 0.1 to 2% of at least trialkylated phenols.

The carbonyl component used may be any saturated aliphatic and cycloaliphatic aldehydes and ketones containing from 1 to 12 and preferably from 1 to 6 carbon atoms. Formaldehyde, acetaldehyde, propionaldehyde, acetone, butanone and cyclohexanone are particularly suitable because of their ready availability.

The reaction according to the invention is normally carried out at atmospheric pressure. In some cases, however, it may be advisable to apply excess pressure in order to make it possible for an optimal reaction temperature to be reached. The reaction generally takes place at temperatures below 120° C. and preferably at temperatures in the range from 50° to 80° C.

The molar ratio of dialkyl phenol mixture to aldehyde or ketone amounts to at least 2:1. The molar ratio has no upper limit for chemical reasons. It depends upon the reactivity of the reactants, the reaction temperatures and the reaction time. Normally, however, a ratio of 40:1 is not exceeded.

The reaction may be carried out in the presence of solvents. It is preferred to use apolar solvents, for example hydrocarbons, such as toluene, benzene or hexane. By adding solvents such as these, the aromatic polyhydroxy compounds can be prevented from crystallising out, even where a slight excess of dialkyl phenol is used.

The process may be carried out either continuously or in batches. In cases where the process is carried out continuously, the reaction may be carried out in a fluidised-bed reactor or, preferably, in a fixed-bed reactor. The continuous reaction is preferred.

The required alkylated aromatic polyhydroxy compounds may be isolated from the reaction mixture in known manner by distillation, extraction or crystallisation. Isolation may also be carried out with advantage by separating off excess phenol and low-boiling substances from the reaction mixture in an evaporator at temperatures in the range from 100° C. To 300° C., preferably in the range from 150° C. to 250° C., and under pressures of from 0.05 to 1000 millibars, preferably from 0.5 to 500 millibars, and subsequently removing the residual monophenols to a content of less than 5% by weight and preferably less than 0.5% by weight of monophenols, based on the residue, by desorption in the corresponding temperature range and in the corresponding pressure range in the presence of an inert gas, particularly nitrogen.

The mixtures of alkylated aromatic polyhydroxy compounds, preferably alkyl bisphenol mixtures, may be used directly as sump products for the production of polycarbonates and the monophenols separated off may be returned to the process according to the invention.

Accordingly, the present invention also relates to the use of the mixtures of aromatic polyhydroxy compounds obtained in accordance with the invention as sump products for the production of high molecular weight thermoplastic polycarbonates by known methods.

It has been found that the use of the mixtures of alkylated aromatic polyhydroxy compounds according to the invention for the production of polycarbonates affords particular advantages. Thus, the solubility of the alkali metal salts of the mixtures of polyhydroxy compounds according to the invention in water is particularly good which is of advantage for the two-phase interface process for the production of polycarbonates. The tendency towards crystallisation of the polycarbonates obtained from the mixtures of polyhydroxy compounds according to the invention is also particularly low which is of importance both in the production of polycarbonates and also in the use of the polycarbonates.

The high molecular weight polycarbonates according to the invention have average molecular weights $\overline{M}_w$ of at least 20,000 and preferably of at least 25,000. Average molecular weights $\overline{M}_w$ of more than 200,000 may be obtained. In general, however, average molecular weights $\overline{M}_w$ of less than 100,000 are preferred for use in the thermoplast sector, average molecular weights below 60,000 being particularly preferred for this purpose.

The polycarbonates according to the invention obtained from mixtures of alkylated aromatic polyhydroxy compounds surprisingly show substantially the same favourable properties as conventional polycarbonates obtained from pure alkylated aromatic dihydroxy compounds. In addition, they even show significant improvements in a number of properties. Thus, they generally show extremely high solubility in organic solvents, particularly lacquer solvents, and in polymerisable monomers such as, for example, styrene, acrylonitrile, vinyl chloride, methyl methacrylate and mixtures thereof, which is of advantage for grafting reactions. Accordingly, they may be used as a basis for the production of graft polymers. In addition, they show improved flow properties in the melt and, hence, higher fluidity and improved structural viscosity. In addition, the crosslinkability of films, for example by electron beams, is improved which is important for various applications, In addition, flameproofing is made easier in many cases by the fact that smaller quantities of flameproofing agents (such as for example co-condensed 2,2-bis (3,5-dibromo-4hydroxy phenyl)-propane) are required for the same degree of flameproofing. In many cases, tracking resistance is also distinctly increased.

The polycarbonates according to the invention obtained from mixtures of alkylated aromatic polyhydroxy compounds are compatible with other polymers in the same way as polycarbonates obtained from pure alkylated aromatic polyhydroxy compounds. This is particularly surprising because it is known that even minor variations in polymers often produce significant variations in compatibility and, hence, in properties.

Thus, for example, the compatibility of polycarbonates based on mixtures of methylated aromatic polyhydroxy compounds with, predominantly, 2,2-bis-(3,5-dimethyl-4-hydroxy phenyl)-propane with polyvinyl chloride (cf. German Offenlegungsschrift No. 2,402,176), with polycarbonates based on 2,2-bis-(4-hydroxy phenyl)-propane (cf. German Offenlegungsschrift No. 2,248,818) and with styrene polymers (cf. German Offenlegungsschrifts Nos. 2,329,585 and 2,329,646) is substantially the same as that of polycarbonates based on the corresponding pure bisphenol. Accordingly, it is also possible to obtain excellent polymer alloys with the polycarbonates according to the invention.

Another important factor is the resistance to hydrolysis of the polycarbonates according to the invention particularly polycarbonates based on mixtures of methylated aromatic polyhydroxy compounds with predominantly 2,2-bis-(3,5-dimethyl-4-hydroxy phenyl)-propane (cf. German Offenlegungsschrifts Nos. 2,063,050 and 2,211,957).

The above-described properties of the polycarbonates according to the invention which may be produced from mixtures of alkylated aromatic polyhydroxy compounds isolated as sump products (see above) are particularly surprising. In these polycarbonates, the favourable properties of the bisphenols, some of which were described earlier on, and the above-mentioned additional improvements in the polycarbonates are even more pronounced.

The polycarbonates according to the invention may readily be processed into mouldings, coatings, fibres, lacquers and films. It is also possible with advantage to use certain alloys with other polymers such as, for example, polyvinyl chloride, styrene polymers and polycarbonates of purified bisphenols. The polycarbonates according to the invention and their polymer alloys may also be used to good effect in mixtures with fillers such as, for example, minerals, sawdust and carbon black, reinforcing materials such as, for example, glass fibres, asbestos and carbon fibres, effect materials, dyes pigments, stabilisers, for example for heat, oxidation and UV stabilisation, lubricants and mould-release agents, flameproofing additives such as, for example, halogenated aromatic compounds, metal oxides and metal salts, and other additives. They may be used with particular advantage for applications requiring good electrical properties, high thermal stability under load, extreme toughness and high resistance to hydrolysis. Thus, they may be used for example for high-quality electrical components, electrical insulating films, pipes for alkaline and acid water, housings, components for the automobile industry and domestic appliances.

EXAMPLE 1

A commercial 2,6-dimethyl phenol containing 92.8% by weight of 2,6-dimethy phenol, 7.2% by weight of o-, m-, p-cresol and less than 0.1% of phenol is passed with acetone (in a molar ratio of 1:15, based on 2,6-dimethyl phenol) and 1°/$_{oo}$ of β-mercaptopropionic acid through a fixed-bed reactor filled with dry acid ion exchanger (sulphonated resin, styrene/divinyl benzene 82/18% by weight-bead polymer) for about 20 hours at a temperature of 70° C.

The reaction solution flowing off from the reactor contains (excluding acetone, water and β-mercaptopropionic acid) 6.5% by weight of cresols, less than 0.1% of phenol, 84.5% by weight of 2,6-dimethyl phenol, 8.1% by weight of 2,2-bis-(3,5-dimethyl-4-hydroxy phenyl)-propane and at least five other at least binuclear components (condensation products) in a total of 0.9% (analysis by gas chromatography after silylation).

The reaction solution is passed continuously through an oil-heated tubular coil evaporator (tube length 3.5 meters, tube diameter 10 mm) at a temperature of 190° C. and under a pressure of 27 mbars.

For separation of the droplike liquid carried along the gaseous 2,6-dimethyl phenol is first passed over a cyclone and a short packed column and then cooled in a condenser being operated at 50° C.

The 2,2-bis-(3,5-dimethyl-4-hydroxy phenyl)-propane, which still contains 1.5% of 2,6-dimethyl phenol, flows from the tubular coil evaporator into a thin-layer evaporator with a rotor as desorber which is heated with oil to 185° C. and operated under the same pressure as the coil evaporator. A stream of nitrogen (6 liters per hour) is introduced into the desorber from below.

The crude bisphenol (180 g/h) is collected in a receiver. It contains less than 0.1% of phenol, 2,6-dimethyl phenol and cresols, 10.2% of unknown components and 84.5% of bis-(3,5-dimethyl-4-hydroxy phenyl)-propane (crude tetramethyl bisphenol A).

The 2,6-dimethyl phenol separated off is replenished by the amount lost to the tetramethyl bisphenol A, rereacted with the necessary quantity of acetone and then worked up in the same way as described above.

Even after 10 repetitions, neither the 2,6-dimethyl phenol nor the diphenyl alkane mixture shows any significant deviation from the first test.

568.8 g of the crude tetramethyl bisphenol A obtained as described above and 5.6 g of phenol are dissolved in 2286 ml of distilled water and 614.4 ml of 45% sodium hydroxide solution. After the addition of 1490 ml of methylene chloride, 448 ml of chlorobenzene, 7.72 g of tetrabutyl ammonium bromide and 5.70 ml of tri-n-butyl amine, 336.4 g of gaseous phosgene are introduced into the mixture with stirring over a period of 60 minutes. After the introduction of 250 g of phosgene, another 96 ml of 45% sodium hydroxide solution are added. Following the addition of 5.6 triethyl amine, the mixture is stirred for 30 minutes. For working up, the organic phase is then acidified with dilute $H_3PO_4$, diluted with methylene chloride and washed with water until free from electrolyte. The polycarbonate obtainable by evaporating off the organic solvent has a relative viscosity $\eta_{rel}$ of 1.296 (as measured at 25° C. on 0.5 g of polycarbonate in 100 ml of $CH_2Cl_2$ solution) and shows excellent properties.

EXAMPLE 2

610 parts by weight of a commercial dimethyl phenol containing 91.1% by weight of 2,6-dimethyl phenol, 8.9% by weight of o-, m-, p-cresol and less than 0.1% by weight of phenol were reacted for 20 hours at 70° C. with 19.3 parts by weight of acetone (in a molar ratio of 1:15, based on technical 2,6-dimethyl phenol), 1°/$_{oo}$ of β-mercaptopropionic acid and 10 parts by weight of concentrated hydrochloric acid in a three-necked flask equipped with a thermometer, stirrer and reflux condenser. The reaction solution contained:

6.9% by weight of cresols, less than 0.1% by weight of phenol, 87.8% by weight of 2,6-dimethyl phenol, 4.5% by weight of 2,2-bis-(3,5-dimethyl-4-hydroxy phenyl)-propane and at least five other binuclear components (condensation products) in a total of 0.7% by weight (analysis by gas chromatography after silylation) not including acetone, water and β-mercaptopropinoc acid as in Example 1.

Even after the commercial 2,6-dimethyl phenol has been used only once, the composition of the residual unreacted 2,6-dimethyl phenol in this Example has changed through reduction in the concentration of the cresols by 1.5% by weight and enrichment of the 2,6-dimethyl phenol by the same amount to such an extent that the unreacted starting compound cannot be re-used with the object of obtaining the same end product with each successive use.

We claim:

1. A process for producing a mixture of alkylated aromatic polyhydroxy compounds suitable for the direct production of high molecular weight thermoplastic polycarbonates which comprise reacting commercial 2,6-dialkyl phenol containing 98 to 70% of 2,6-dialkyl phenol, 2 to 30% of monoalkyl phenol, about 0.1 to 5% of phenol and about 0.1 to 2% of an at least trialkylated phenol with a carbonyl compound in the presence of a catalytic amount of an acidic organic ion exchanger and recycling into the reaction unreacted commercial 2,6-dialkyl phenol without intermediate purification.

2. A process for the production of mixtures of alkylated aromatic polyhydroxy compounds as claimed in claim 1, wherein these compounds are recovered by separating off excess phenol and low-boiling substances from the reaction mixture in an evaporator at temperatures in the range from 100° C. to 300° C. and under pressures in the range from 0.05 to 1000 millibars, and the residual monophenols are removed to a content of less than 5% by weight, based on the residue, by desorption in the corresponding temperature range and in the corresponding pressure range in the presence of an inert gas, particularly nitrogen.

3. Mixtures of alkylated aromatic polyhydroxy compounds obtained by the process claimed in claim 1.

* * * * *